(12) United States Patent
O'Farrell et al.

(10) Patent No.: US 10,160,966 B2
(45) Date of Patent: Dec. 25, 2018

(54) SAMPLE PREPARATION METHOD AND APPARATUS

(71) Applicant: ALTRATECH LIMITED, Limerick (IE)

(72) Inventors: Brian O'Farrell, Watergrasshill (IE); Timothy Cummins, Cratloe (IE); Cian Desmond O'Sullivan, Limerick (IE); Jorge Álvarez-Vicente, Cork (IE)

(73) Assignee: ALTRATECH LIMITED, Limerick (IE)

( * ) Notice: Subject to any disclaimer, the term of this patent is extended or adjusted under 35 U.S.C. 154(b) by 30 days.

(21) Appl. No.: 15/101,200

(22) PCT Filed: Dec. 10, 2014

(86) PCT No.: PCT/EP2014/077168
§ 371 (c)(1),
(2) Date: Jun. 2, 2016

(87) PCT Pub. No.: WO2015/086652
PCT Pub. Date: Jun. 18, 2015

(65) Prior Publication Data
US 2016/0298107 A1    Oct. 13, 2016

(30) Foreign Application Priority Data
Dec. 12, 2013 (EP) .................................... 13197017

(51) Int. Cl.
*C12N 15/10* (2006.01)
*C12Q 1/6806* (2018.01)

(52) U.S. Cl.
CPC ....... *C12N 15/1013* (2013.01); *C12Q 1/6806* (2013.01)

(58) Field of Classification Search
CPC ......... C12Q 1/68; C12Q 1/6806; C07H 21/04
See application file for complete search history.

(56) References Cited

U.S. PATENT DOCUMENTS

| | | | | |
|---|---|---|---|---|
| 6,428,962 B1 * | 8/2002 | Naegele | ............. | C12N 15/1003 435/6.1 |
| 8,623,636 B2 * | 1/2014 | Fernandez Lopez | .. | B82Y 15/00 427/214 |
| 2003/0059789 A1 | 3/2003 | Efimov et al. | | |
| 2004/0086944 A1 * | 5/2004 | Grigg | ................... | C12Q 1/6809 435/7.1 |
| 2004/0161788 A1 | 8/2004 | Chen et al. | | |
| 2011/0124851 A1 | 5/2011 | Guo | | |

FOREIGN PATENT DOCUMENTS

| | | | |
|---|---|---|---|
| EP | 1 944 368 A1 | | 7/2008 |
| WO | WO 2006/071770 | * | 7/2006 |

OTHER PUBLICATIONS

Walsh et al, Chelex 100 as a Medium for Simple Extraction of DNA for PCR-Based Typing from Forensic Material, 1991, BioTechniques, 10, 506-513 (Year: 1991).*
Vaara, Maarti; "Agents That Increase the Permeability of the Outer Membrane"; Microbiological Reviews; vol. 56, No. 3; Sep. 1992; pp. 395-411.
International Search Report issued in PCT/EP2014/077168; dated Mar. 2, 2015.
Michele K. Nishiguchi et al.; "DNA Isolation Procedures"; Methods and Tools in Biosciences and Medicine, Techniques in molecular systematics and evolution; 2002; pp. 249-287; Birkhäuser Verlag Basel/Switzerland.
International Preliminary Report on Patentability and Written Opinion of the International Searching Authority; PCT/EP2014/077168 dated Jun. 14, 2016.
http://www.bio1000.com/experiment/biochemical/241859.html; "Bio Information, Mechanism and Steps of Separating and Purifying DNA with Magnetic Beads"; 3 pp.; May 22, 2012.
Office Action issued by the Chinese Patent Office dated Jul. 24, 2018 for Chinese Patent Application No. 201480075445.4; 12 pp.

* cited by examiner

*Primary Examiner* — Narayan K Bhat
(74) *Attorney, Agent, or Firm* — Studebaker & Brackett PC

(57) ABSTRACT

A method of preparing a nucleic acid sample with target enrichment uses a reaction vessel (11), within which is added a chelating agent to a sample with heating to about 99° C. to provide a crude lysate. A PNA probe is provided at a concentration sufficient for binding and capture of discernible levels of target nucleic acid. The PNA probe may be attached to beads (26) which are initially embedded in a wax body (17) and are released during the heating so that they are free to move and come into contact with the PNA probe and target DNA. After binding has occurred, the beads are magnetically attracted back into a pocket (16) along with the wax (17), which is allowed to solidify before they are removed from the reaction vessel.

22 Claims, 6 Drawing Sheets

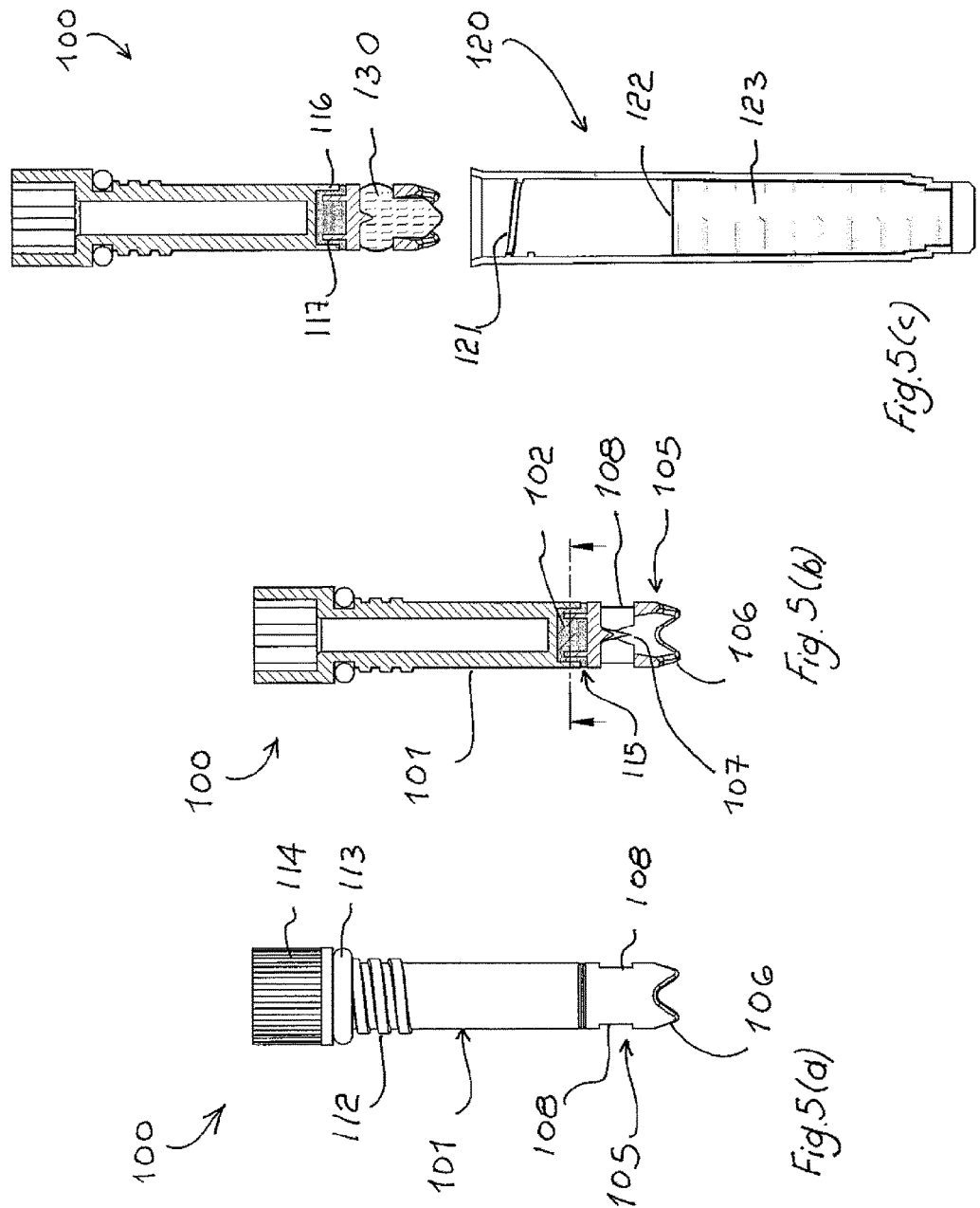

SAMPLE PREPARATION METHOD AND APPARATUS

INTRODUCTION

The invention relates to preparation of samples for analysis, such as tissue or blood samples, or any other sample having nucleic acid (NA), (e.g. DNA or RNA).

Isolating and purifying NA of interest from a sample is a critical step in molecular biological applications in the fields of forensics, food safety, medicine etc. Sample lysis and whole nucleic extraction techniques are frequently complex; time consuming; require skilled technicians or robotics; require expensive consumables; and increase the risk of cross-contamination. Complexity poses problems for manual and automated systems alike with simpler systems often being more robust. Co-precipitation of salts (which may inhibit downstream chemical reactions) and NA overloading of glass microfiber filters when extracting from larger amounts of sample are common problems. Excessive DNA can inhibit PCR due to sequestering $Mg^{2+}$ required for amplification. This limits the amount of a total NA extraction which can be used which is troublesome where the target DNA is relatively rare within the extraction. Total NA extraction is unnecessary for the majority of genetic testing. Purification of sequences of interest would be preferable in many cases. Additionally, many techniques work well (PCR) or even demand shorter NA templates (e.g. next generation sequencing).

Multiple liquid handling steps can result in loss or uneven extraction efficiencies of different DNAs or RNAs. µRNAs are becoming more important in early identification of disease due to changes in their expression, however µRNA-specific kits are expensive, and µRNA's may be lost in many extraction techniques due to their small size (18-24 bp). Poly(T) probes are sometimes used to selectively capture messenger RNA (mRNA) from total RNA extractions. The enriched fraction of mRNA may then be sequenced to analyse the relative expression of different genes (exome analysis). This expression profile contains valuable information for agricultural and medical diagnostics, or response of tissue cultures to novel drug therapies. However, mRNA is just 1-5% of total RNA (~80% is ribosomal RNA), and current extraction methods are liable to lead to loss of rare material or to change the relative frequencies of different sequences. RNA, additionally, is particularly liable to damage, commonly by ubiquitous environmental RNAse. Simple and rapid extraction of target NA of interest (particular rare or vulnerable species such as mRNA) will improve the quality of analysis downstream. Finally, existing kits targeting mRNA are typically expensive (more than € 25 per sample). Given developments in genetic analysis technology, such sample preparation costs are an important barrier to making these technologies available to users in the industrial and medical sectors.

US2003/0059789 (Efimov et al) describes oligonucleotide analogues, methods of synthesis and methods of use. It uses PNA in target enrichment.

US2004/0161788 (Chen et al) describes a sample processing tubule with three segments. It appears to describe a complex multi-reagent step, multi-chamber, and multi-valve system. A chelating agent, namely, EDTA is mentioned. This is apparently as an anti-coagulating agent in some examples, and in other examples it is used after DNA extraction during target enrichment.

Michele K. Nishiguchi et al: "DNA Isolation Procedures" 1 Jan. 2002, Birkhauser Basel, Basel ISBN 978-3-03- 488125-8 pages 249-287 describes various DNA isolation procedures. This teaches several DNA isolation methods including adding a buffer comprising Chelex™ and EDTA, i.e. two chelating agents, to the sample and heating at 100 C for 12 min (p 265-266: "protocol 4").

There is a requirement for an improved method and apparatus for simple, rapid NA extraction, which minimises the risks of cross-contamination and loss of NA during processing and sampling. Another objective is that there are fewer steps and less time for sensitive NA (especially RNA) to be damaged. Another objective is that it should target only the sequences of interest in large samples or mix of sequences, or the mRNA portion of total RNA. Another objective is that the method and apparatus be simple, repeatable and reproducible, and capable of effective sequence-specific target nucleic acid extraction and purification directly from a large mesofluidic sample with minimal user input.

The invention is directed towards achieving some or all of the above objectives

SUMMARY OF THE INVENTION

According to the invention, there is provided a method of preparing a nucleic acid sample for analysis with target enrichment, the method comprising the steps of:
(a) in a reaction vessel, adding a chelating agent to the sample until cells are lysed, to provide a crude lysate, and
(b) providing a PNA probe at a concentration sufficient for binding and capture of discernible levels of target nucleic acid.

According to another aspect of the invention, there is provided an apparatus for preparing a nucleic acid sample for analysis with target enrichment, the apparatus comprising a reaction vessel, a device for adding a chelating agent to a sample in the vessel until cells are lysed, to provide a crude lysate, and a device for providing a PNA probe at a concentration sufficient for binding and capture of discernible levels of target nucleic acid. The apparatus may also have features for performing any of the steps defined below.

In one embodiment, the sample is heated with the chelating agent.

In one embodiment, the method comprises the step of providing beads to which the PNA probes attach. Preferably, the beads are provided after the cells are lysed and the PNA probes have had time to bind to the target nucleic acid. In one embodiment, the beads are paramagnetic or magnetic. In one embodiment, the beads are in the size range of 50 nm to 5 µm.

In one embodiment, the PNA probe is attached to the inside of the reaction vessel or is in solution within the vessel. In one embodiment, the PNA probe and the crude lysate are brought into contact after the crude lysate cools to below a lysate annealing temperature (e.g. 63° C.).

In one embodiment, the step (a) is performed so that the target nucleic acid is sheared into fragments. In one embodiment, the sample is partially or fully caused to flow by magnetic attraction.

In one embodiment, the chelating agent concentration is in the range of 1% w/v to 20% w/v with respect to the sample.

In one embodiment, the chelating agent is a styrene-divinylbenzene co-polymer containing iminodiacetic acid groups, such as Chelex™ 100 resin (BioRad).

In one embodiment, the heating is at a temperature of 70° C. to 99.5° C., and preferably in the range of 98° C. to 99.5° C. for at least 5 minutes to provide a sample pH in the range of 10 to 11.

In one embodiment, the beads are magnetically removed after target nucleic acid has attached to the PNA probes. In one embodiment, the beads are removed on a surface in the magnetic field of the magnet. In one embodiment, the beads are removed in a recess or pocket of a body in the magnetic field of the magnet. In one embodiment, the pocket includes a carrier of oil or a wax. In one embodiment, the oil or wax is in liquid form during the reaction without application of a magnetic field, and is caused to solidify after the magnetic field has been applied and the beads have been attracted into the pocket. In one embodiment, the oil or wax is molten due to applied heating for lysing. In one embodiment, the oil or wax is located so that its temperature does not reach the lysing temperature, rather a lower temperature which causes the oil or wax to melt to free the beads.

Preferably, the oil or wax is located at the surface of the sample, and heating is applied at the lower end of the vessel, whereby the oil or wax remains on top of the surface while molten due to floating.

In one embodiment, the vessel is elongate and upright, heat is applied to the vessel at its lower end, and the oil or wax body is supported at or near the surface of the sample in the vessel.

In one embodiment, the oil or wax body is supported in a pocket at the lower end of an insert within the vessel, and the insert also comprises a magnetic device for applying and withdrawing a magnetic field.

In one embodiment, the insert has an internal conduit within which a magnet may be moved from a spaced-apart position to a position sufficiently close to the pocket so that it applies a magnetic field to the oil or wax body. In one embodiment, the wax or oil comprises a biphasic and thermomorphic body of oil or wax and water including an ionic liquid which varies in miscibility with water depending on a physical parameter such as temperature or pH.

In one embodiment, an anion or cation of an ionic liquid has a functional group which is the chelating agent, in which the functional group captures target cations from an aqueous solution when the ionic liquid is water miscible, and in which a change in physical parameters changes the miscibility of the ionic liquid, and in which the ionic liquid, functional group and any captured target analyte is shifted between phases, providing for removal.

In one embodiment, the anion or cation of the ionic liquid has a functional group which is a PNA, in which the functional group captures target nucleic acids from an aqueous solution when the ionic liquid is water miscible, and in which a change in physical parameters changes the miscibility of the ionic liquid, and in which the ionic liquid, functional group and any captured target analyte are shifted between phases in this manner, providing for extraction and purification of target analyte.

In another aspect, the invention provides a microbiological sample preparation apparatus comprising:
a reaction vessel,
a heater to heat the vessel at a lower end of the vessel to a level sufficient to lyse a sample with an analyte in the vessel,
a probe,
a support holding a body of solid oil or wax with embedded paramagnetic or magnetic beads having a coating for attracting the probe,
wherein the probe is immobilised on a surface of the support and/or the oil or wax body and/or the vessel internal surface,
a magnetic device for applying a magnetic field to attract the beads to the support after incubation when the wax or oil body is molten.

In one embodiment, the apparatus is configured for removing the support from the vessel to remove the beads as they are embedded in the wax or oil body after said body has re-solidified and/or because they are attracted to the support by a magnetic field.

In one embodiment, the magnetic device comprises a conduit within the support within which a magnet may be moved between a position proximate to the support lower end and a spaced-apart position. In one embodiment, the support has a pocket with a downwardly-facing open face within which the oil or wax body is engaged. In one embodiment, the apparatus comprises a device for analysing the analyte without removing the analyte.

Preferably, the support includes, at an upper end, said analysis device. In one embodiment, the analysis device includes a loop mediated amplification device. In one embodiment, the analysis device includes a capacitive sensor. In one embodiment, the analysis device includes an optical sensor.

In one embodiment, the support is a stem which is configured with a head for removing the sample from a material.

In one embodiment, the stem comprises a tip with a recess, at least one receiver in a side wall of the recess, and a guide in the recess for pressing material radially into the receiver as the tip is pressed into the material. In one embodiment, the guide is a distally-pointing spike and the receiver is an opening in the wall of the recess. In one embodiment, the head is separable from the stem being joined by an interlock which requires a friction fit of interlocking solid parts with solid wax in-between, but melting of the wax causing separation so that the head drops to a bottom of the vessel.

In another aspect, the invention provides a method of preparing a microbiological sample, the method comprising the steps of:
depositing the sample into a reaction vessel,
heating the vessel at a lower end of the vessel to a level sufficient to lyse the sample,
providing a probe,
holding at a surface of the sample a body of solid oil or wax with embedded paramagnetic or magnetic beads having a coating for attracting the probe,
heating the wax or oil body so that the oil or wax becomes molten and the beads are free to mix in the sample,
applying a magnetic field to attract the beads to the support after incubation when the wax or oil body is molten.

In one embodiment, the method comprises the step of removing the support from the vessel to remove the beads as they are embedded in the wax or oil body after said body has re-solidified and/or because they are attracted to the support by a magnetic field.

In one embodiment, the heating to lyse the sample occurs at a position in the vessel lower than the wax or oil plug, and said heating is sufficient to lyse the cells at a lower vessel level, and to melt the wax or oil at a higher vessel level. In one embodiment, the method comprises analysing the analyte without removing it from the vessel of the support.

DESCRIPTION OF THE DRAWINGS

The invention will be more clearly understood from the following description of some embodiments thereof, given by way of example only with reference to the accompanying drawings in which:—

FIGS. 5(a) to 5(f) is a series of diagrams showing a sampling apparatus of another embodiment

DETAILED DESCRIPTION OF THE EMBODIMENTS

The invention in some embodiments employs peptide nucleic acids (PNAs) as probes. PNAs are synthetic polymers with a N-(2-aminoethyl)-glycine backbone linked by peptide bonds and purine and pyrimidine bases bonded by a methylene bridge (—CH2-) and a carbonyl group (—(C═O)—) allowing them to engage in Watson-Crick bonding with other PNAs and NAs. PNAs were developed originally as a type of drug which would target messenger RNA and affect gene expression but later have shown value in NA hybridisation procedures. PNAs are resistant to extremes of pH and degradation by nucleases. The specificity of PNA probe binding allows shorter probes to be used also, making them particularly useful for the binding of μRNAs. As they have no charge, they do not need the benefit of cation screening to allow them to engage in Watson-Crick binding with PNAs or NAs.

Chelex™ extraction results in low ionic content. When ionic concentration is low, binding of two complementary nucleic acid strands is difficult as both have a negative charge and tend to repel each other without shielding of this charge by cations. This results in single stranded DNA and, prevents the use of DNA or RNA probes for target enrichment from Chelex™ extractions. This low ionic solution, the high pH and the shearing of NA during Chelex™ extraction are broadly considered serious disadvantages of this type of extraction. However, the problem is overcome, and these disadvantages turned to advantages, by using a PNA probe. PNA probes bind to complementary DNA and RNA sequences with high specificity, even in low-ionic/high-pH solution. The unusual but advantageous combination of Chelex™ extraction and PNA probes provides for a rapid, sequence-specific nucleic acid extraction procedure.

It is preferred that the timing of the steps is:
(a) initially provide the PNA probes, then
(b) lyse the cells so that the Chelex™ and low ionic solution ensures that the NA is single-stranded and available for binding with the PNA probes, and
(c) finally, provide the beads to bind with the PNA probes.

Figure 1:
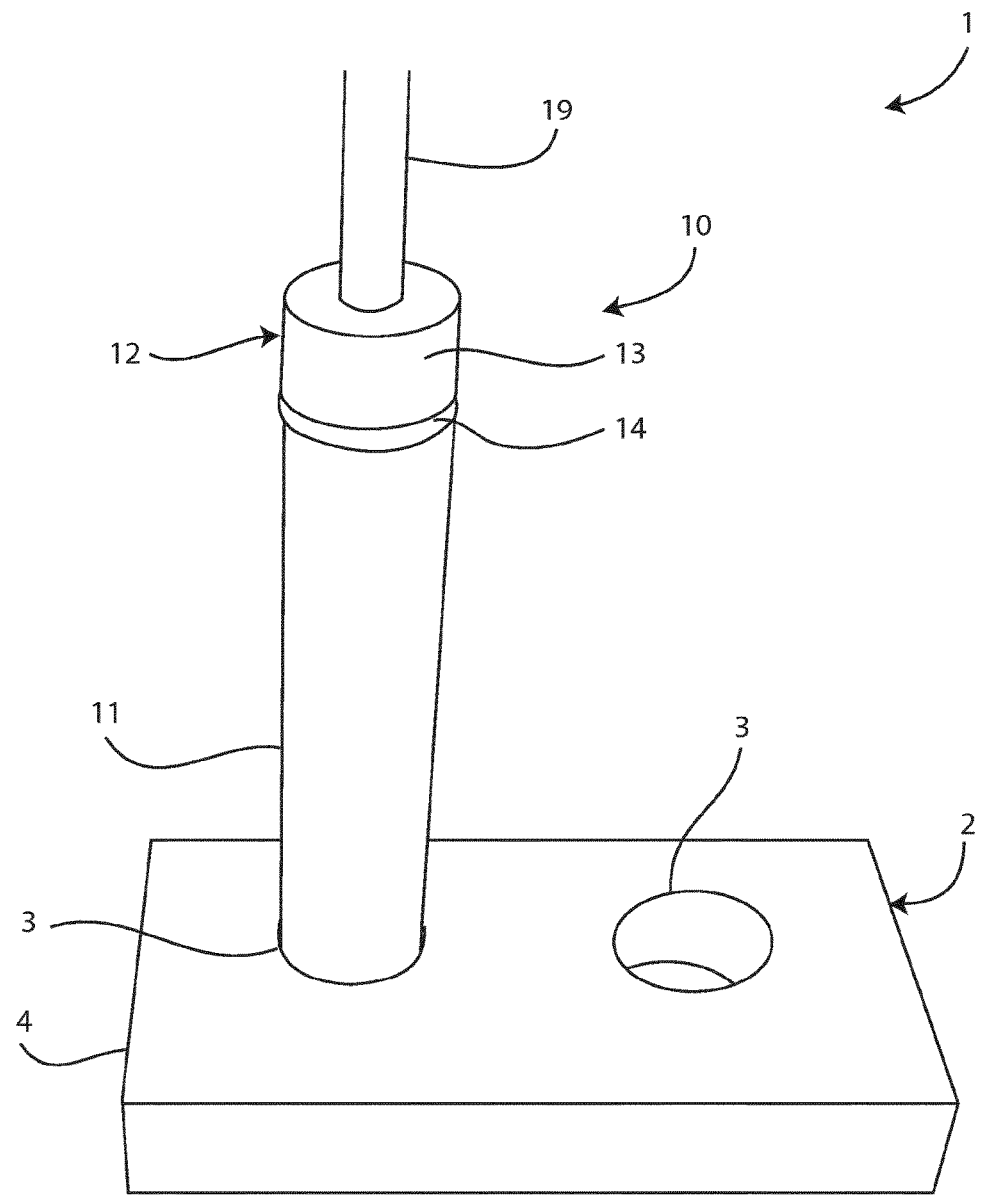
FIG. 1 is a perspective view of a sample preparation apparatus of the invention.
Figure 2:
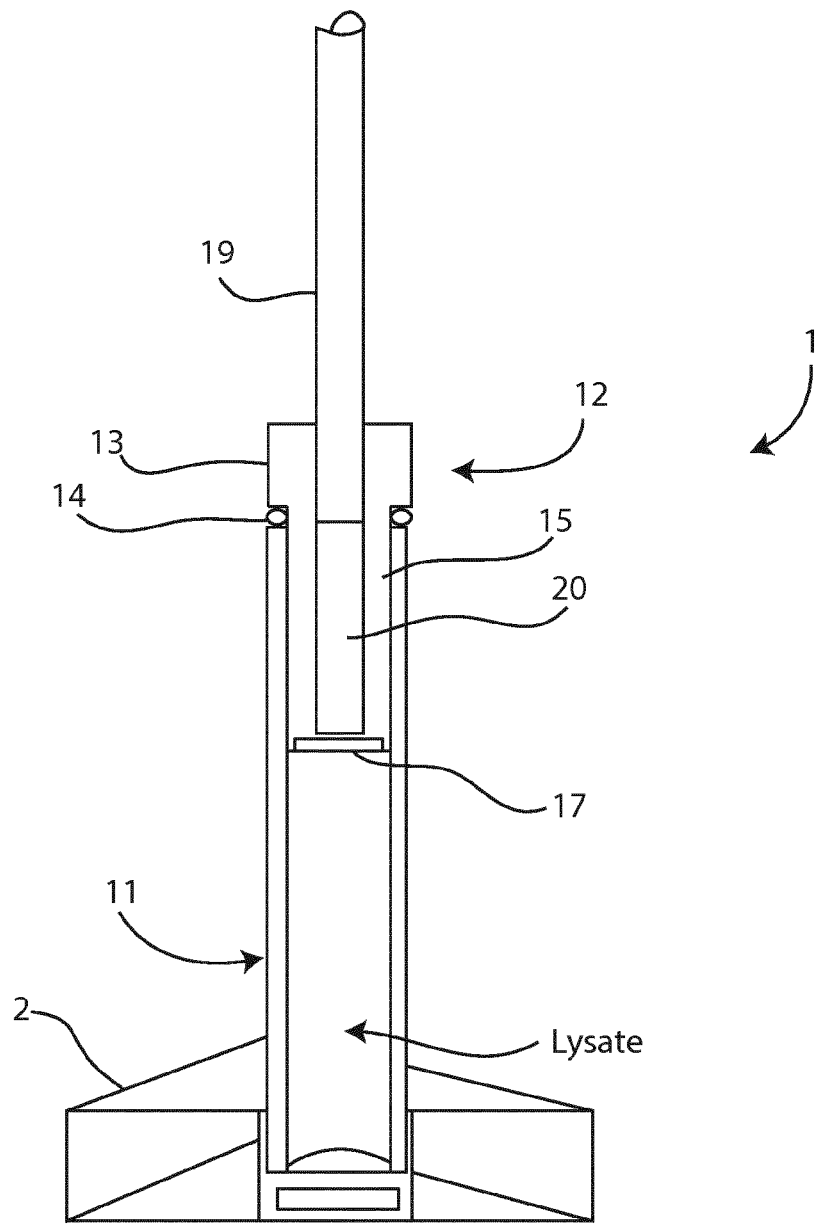
FIG. 2 is a diagrammatic cut-away view showing the internal components.
Figure 3:
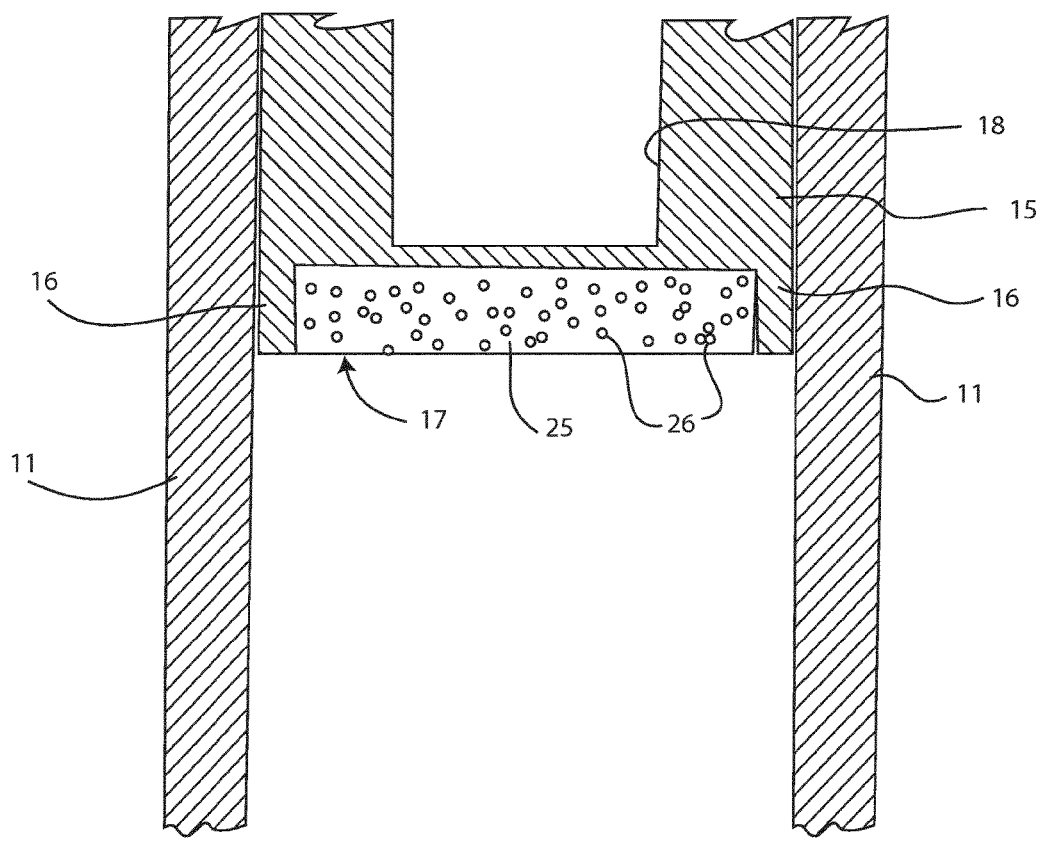
FIG. 3 is an enlarged and cross-sectional view showing particular detail of a wax plug with embedded beads.

Referring to FIGS. 1 to 3 a sample preparation apparatus 1 is illustrated. The apparatus 1 comprises a base 2 with a heat exchange housing 4 having recessed seats 3 for one or more self-contained sample preparation devices 10. Each device 10 comprises a tubular housing 11 the top opening of which is closed by a cap 12 having a body 13 with a shoulder overlying an O-ring seal 14. A lower part of the cap body 13 is in the form of an insert 15 which extends down into the tubular housing 11 as a continuation of the cap body 13. At its lower end the insert 15 forms a downwardly-facing recess 16 housing a wax plug 17. Also, the body 13 has a blind hole 18 which extends down through it, terminating about 0.5 mm from the recess 16.

The device 10 also comprises a rod 19 which is configured to move vertically through the bore 18, carrying a magnet 20 at its lower end. This allows the magnet 20 to come into close proximity to the wax plug 17 but separated by the short solid plastics gap between the bottom of the bore 18 and the recess 16.

As is described in more detail below, the wax plug 17 is formed of wax 25 within which are uniformly distributed magnetic beads 26 having a coating (e.g. streptavidin) to bind to a probe which is selected for attracting a target NA within the volume formed below the plug 17 within the tubular housing 11. This volume contains lysate and the wax plug 17 is a friction fit within the recess 16. The plug 17 is a disc-shaped body of wax 25 (e.g. molecular grade paraffin wax) within which are embedded the paramagnetic beads 26, a known composite of polystyrene and ferrite nanoparticles.

Sample Preparation Method Main Steps

The following describes a sample preparation method of the invention performed using the apparatus 1. Typical times for each step are given in parentheses. It will be appreciated that the method may alternatively be performed with use of a different apparatus, possible without some of the benefits of the apparatus 1 such as the closed environment throughout sample preparation.

A sample of interest is added to the vessel 11 containing Chelex™ 100 (5-20% w/v) and water (e.g. deionised water). The vessel is then capped 12. The sample may, for example, have a carrier liquid carrying an analyte and the liquid level is up to the base of the plug 17. (1 min)

As noted above, the streptavidin-coated paramagnetic beads 26 are held within the wax plug 17 in the pocket 16. The surface of the cap 12 and plug 17, as are now below the liquid level, are coated in lyophilised, biotinylated PNA probes complementary to the sequence of interest. The PNA probes then go into solution as they are freed from the surface. The lower end of the sealed vessel 11 is heated by the base 2 to 99° C., resulting in a crude lysate. Convective heating melts the wax 25 (e.g. greater than 60° C.) but the beads 26 are held in situ by the magnet 20 (5 mins).

The temperature at the base is reduced to the annealing temperature of the PNA probe and the NA of interest, allowing binding. This temperature is 63° C. (3 mins). The magnet 20 is removed and the higher density and hydrophilic beads 26 drop out of the wax plug 17 and enter into the lysate where they circulate and bind biotinylated PNA probes and any captured target NA. (5 mins). The magnet 20 is re-inserted through the bore 18 and the circulating beads 26 are re-captured at the top of the volume, generally within the recess 16 (1 min). Target NA are now safely transported by the beads (hence "T-beads"), and concentrated within the wax plug 17. The cap 12 is removed from the vessel 11, with the wax/bead. The PNA probe/target NA mixture is magnetically held within the recess 16. This is transported to an analysis station. Advantageously, because of the embedding in wax there is little chance of contamination. At the analysis station, separation is provided by PNA-NA Watson-Crick binding, biotin-streptavidin binding and paramagnetic beads (1 min).

It will be appreciated from the above that the entire sample preparation procedure was completed in about 15 minutes, and without opening the vessel 11 from the moment the sample was introduced. Also, the heating provides the effect of lysing at a lower part of the vessel 11 at a temperature of about 70° C. to 99.5° C., and preferably in the range of about 97° C. to about 99.5° C. However at the higher levels closer to the plug 17 the temperature is lower, about 55 to 65° C. This is sufficient to melt the wax to free the beads 26, but the wax remains on top as it is lighter than the underlying liquid and so floats. Also, the temperature differential provides mixing by way of convention within the vessel 11. This convection is sufficient to thoroughly mix the components to maximise contact of target NA with the probe and of the probe to the beads 26. However, this circulation is not sufficient to equalise the temperature. This is because the vessel 11 has a high aspect ratio.

In more detail, the paramagnetic beads ("T-beads") 26 are of ~2.8 μm diameter and are streptavidin-coated. In general it is preferred to have a bead size in the range of 100 nm to 5 μm.

The beads 26 are well dispersed within the wax 25. The cap is in a sterile packet. A pack of caps may also come in a sterile packet (e.g. X96).

Sequence-specific PNA probes are provided lyophilised on the surface of the recess 16 and the vessel 11.

The base 2 in this embodiment includes a Peltier device for heating and cooling.

The vessel 11 is of polypropylene SBS, is 2D barcoded, and is of 1.4 ml capacity. This tube has a height of 40 mm and an internal diameter of 8.5 mm and a wall thickness of 1 mm, and so is suitable for convective heating. The tube 11 is pre-filled with 1 ml (liquid column 29.5 mm high with 10.5 mm air above, range 100-1300 μl) of a lysis buffer containing 10% w/v (range 5-20%) Chelex™ 100 resin (BioRad). Chelex™ is a styrene-divinylbenzene co-polymer containing iminodiacetic acid groups. It helps to purify other compounds by ion exchange and can bind transition metal ions. Chelex™ solutions are alkaline (pH 8.4-10) and, this, together with heating (e.g. 99° C.) provide for efficient sample lysis. However, enzymes called nucleases which break down NA are also released in cell lysis. Chelex™ resin additionally scavenges metal ions required (cofactors) by the nucleases to function, protecting NAs from degradation. The user removes a foil seal and adds the sample (e.g. a narrow 1 μl plug of tissue taken with a unicore from a cattle carcass).

The single piece, injection-moulded, sterile, polypropylene cap 12 fits into the tube 11. The cap 12 has a screw head and rubber O-ring 14 (both 8.5 mm diameter) to seal firmly into the tube 11. The portion of the cap 12 screwed into the tube 11 is 11.5 mm in height and has a 7.0 mm external diameter. The recess 16 will, thus, be immersed in the lysis solution. The insert 15 is cylindrical of 3 mm diameter and extends 10.5 mm, with the base thus sealed from the lysis buffer. The rod 19 is manually inserted into the hole 18 and holds a small neodymium magnet 20 (e.g. Apex Magnets 12.0 mm×3.0 mm magnet). The recess 16 has a 7.0 mm external diameter, a 6.5 mm internal diameter and depth of 1 mm. The recess or pocket is filled with the plug 17 which is of suitable wax (e.g. Molecular Grade Paraffin Wax) which will melt at moderately high temperatures (e.g. >45° C.). The T-beads 26 are held in situ and prevented from clumping during storage by being dispersed within the solid wax 25. This removes the need for blocking and washing of beads before use, as may be a problem in many existing systems employing beads. The PNA probes are lyophilised on the surface of the plug 17 and cap 12.

The cap 12 is engaged with the tube 11, sealing the tube during the lysis step. The bottom end of the cap 12 is immersed in the lysate. This results in the lyophilised PNA probe entering into solution. The capped tube 11/12 is placed on the heating plate 2 at 99° C. An advantageous heat differential between the bottom and top of the tube occurs. Tissue in the 99° C. zone at the base is lysed. The top of the volume reaches a temperature of about 72° C. which readily melts the wax plug 17 but does not cause damage to the streptavidin. The beads 26 are held in situ by the magnet 20, protected from the high pH in the lysate. After a five minute lysis step and the release of NA, the temperature is dropped at the base of the tube to the annealing temperature of the PNA and NA of interest (e.g. 63° C.). Raleigh-Bénard convection and the presence of PNA and NA of interest in free solution provides for good reaction kinetics and PNA-NA binding during a three minute incubation step.

The wax 25 is still molten at this temperature. The rod 19 and the magnet 20 are removed. The higher density and hydrophilic nature of the T-beads 26 causes them to drop into the lysate. Convection of the T-beads, PNA probes and target NA provides for good reaction kinetics over a three minute incubation step. The biotinylated probes and bound target NA are captured on the streptavidin-coated T-beads. The rod 19 and the magnet 20 are re-engaged. T-beads 26 are drawn into the molten wax 25 by the external magnetic field as they flow around the lysate. After one minute, the tube 11 may be removed from the base plate 2. The wax 25 solidifies with the T-beads 26, PNA probes and target NA separated from the lysate and sealed safely within the wax. This enriched target NA can be stored safely, making it useful for bio-banking.

If required, the cap 12 can now be removed from the tube 11 and placed in another vessel. The encapsulation in wax helps prevent environmental contamination during transfer. The cap 12 is placed in a 0.5 ml 2D barcoded elution tube filled with deionised water at >80° C. The wax 25 will melt at this temperature. The rod 19 and the magnet 20 are disengaged. The beads 26 drop into the second tube where the PNA/NA Watson-Crick binding will melt and the NA is eluted. The beads are drawn back into the receptacle where they will again be captured in the wax.

The above assay and barcoded tube apparatus is particularly amenable to robotic automation, both for a single well design and a standard SBS footprint 96 well format. An array of the caps 12 can be screwed into racks of tubes 11, each containing sample. Similarly, an array of 96 rods 19 and magnets 20 can be automatically engaged and disengaged as required by the assay with a temperature-controlled baseplate.

Our invention rapidly extracts and concentrates target NA in a device which allows reproducibility, and ease of storage and transfer to other vessels. After sample addition, the user-friendly device is completely sealed during the few steps remaining to complete the procedure, reducing the risk of errors and cross-contamination. All reagents are integrated into the device.

In another embodiment, the elution vessel is replaced by an analytical vessel with which the recess 16 engages. In this embodiment, the wax is melted (>45° C.) to create a fluid-fluid interface through which the intact T-bead-PNA-NA complex is drawn into the analytical vessel. The single stranded nature of captured DNA means downstream reactions such as isothermal Loop-mediated amplification (LAMP) would not require an initial denaturation step. The base plate 2 can control isothermal LAMP at 60° C. if the analytical vessel were integrated into the cap 12.

In another embodiment, an extra set of beads (R-beads) with covalently bound probes for a second locus near (~100-5000 bp) which is targeted by the probes on the T-bead may be included in the wax plug. This results in the second beads becoming tethered to the T-beads. This arrangement gives extra specificity and allows haplotype inference. The second beads are too small to overcome interfacial tension and are not drawn into the wax plug unless tethered to the T-beads. The number of R-beads captured in the wax pug (1106) in the removable sampling device is informative for downstream assays.

In another embodiment, the R-beads bind to distinct, complementary PNA probes on a multiple sensor silicon chip built into the device. The chip can be rinsed with deionised water without affecting PNA binding because PNA-DNA or PNA-PNA binding does not require the screening effect of cations. Isolated bead complexes can be stored in situ for bio-banking. The chip may be read later with the number of captured beads on each sensor conveying information on the number of each target NA present in the sample and relative concentration of each. The chip has enough sensitivity to detect captured beads (and hence captured NA) without any amplification of NA being required. This eliminates enzymatic steps (e.g. PCR), significantly simplifying the chemistry in this sample-preparation invention.

Figure 4:
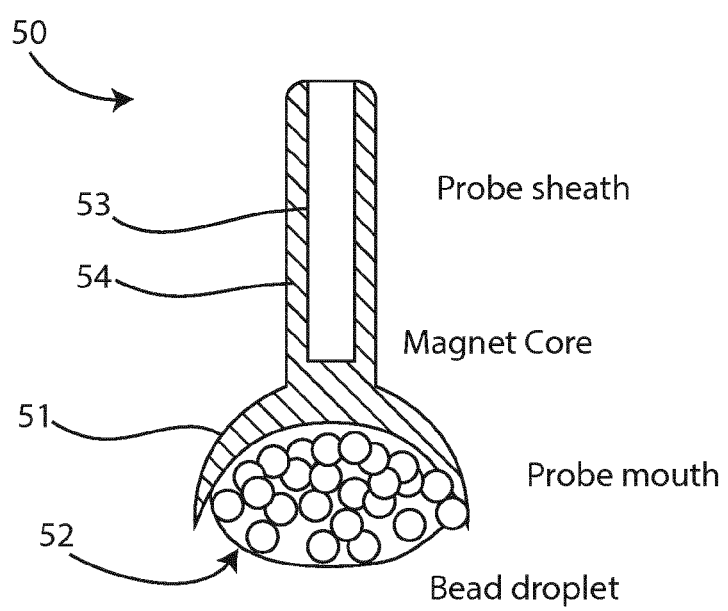
FIG. 4 is a diagram showing an apparatus for bead removal.

Referring to FIG. 4 an apparatus 50 is provided for gathering beads 52 from a liquid in a vessel. It has a stem 54 with an internal bore within which a magnet 53 moves for engagement and disengagement with the beads 52 while they are gathered in a concave head 51. The concave shape is advantageous because it allows a large number of beads to be withdrawn in a tight and compact configuration.

Figure 5F:
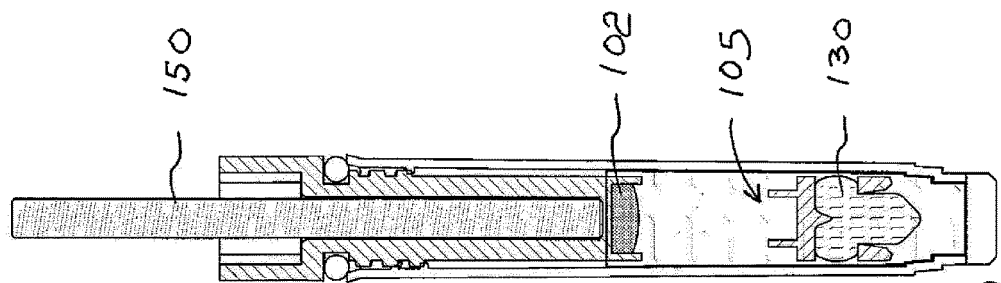
Figure 5E:
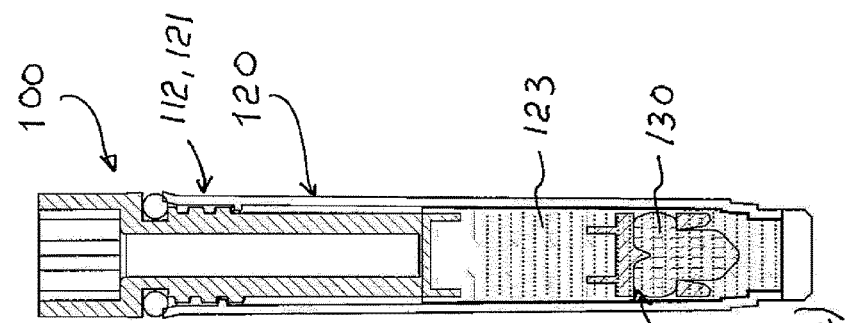
Figure 5D:
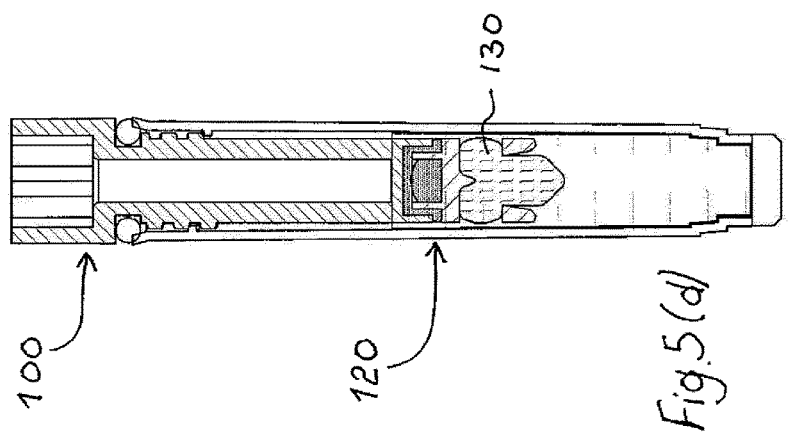

Referring to FIG. 5 an apparatus 100 has a stem 101 with a wax body 102 with beads. There is a separate head 105 with teeth 106, a spike 107 within the head 105 and there are two windows 108.

The head 105 is connected to the stem 101 by an interlock 115 (best illustrated in FIG. 5(b)) with an outer circular ridge 116 on the stem 101 and an inner ring 117 on the head 105. These are manufactured so that they interlock with a friction fit in the presence of the wax 102 when solid. When so interconnected they form a unitary device for taking a sample from a material 130 such as a meat carcass.

The head 105 is pressed into the material and is twisted so that the tapered sides of the spike 107 force tissue 130 out into the windows 108, which grip it as the device is removed.

The device 100 is placed in a receptacle 120 as shown in FIGS. 5(c) to 5(f), the receptacle 120 having a lysis buffer 123 beneath a breakable membrane 122. The receptacle 120 is heated, the wax 102 melts causing the head 105 to separate from the stem 101. As it falls down it takes the unwanted bulk material, leaving the required DNA to attach to the beads and migrate upwards under the influence of a magnet 150. When the stem is placed in the tube 120 containing the lysis buffer 123 the windows 108 provide for better contact between the sample and the lysis buffer 123 during sample lysis. The mechanism is similar to that described above for the apparatus 1.

This apparatus 100, 120 has the advantage of acting initially as a sampling device to remove a small sample of material and then as a testing device. This makes the process of taking a sample simpler, speedier and safer, as metal scalpels and forceps are not required for taking the sample. It also standardises the amount of tissue removed, helping to also standardise the concentration of DNA and RNA in the lysate, which is useful for downstream analysis. Advantageously, all the components of the device 100, 120 are together upon sealing.

In various embodiment, the chelating agents (e.g. iminodiacetic acid) are functional groups of an ionic liquid (cf Pierre Bonhôte,*, Ana-Paula Dias, Nicholas Papageorgiou, Kuppuswamy Kalyanasundaram, and Michael Grätzel (1996) Inorganic Chemistry 35 (5), 1168-1178) which is denser than water and forms a bi-phasic system at room temperature but is miscible at higher temperatures. The chelated cations (e.g. $Ca^{2+}$ and $Mg^{2+}$) are retained in a layer which is denser than the aqueous lysate.

In one embodiment, a PNA probe is the functional group of an ionic liquid of an ionic liquid (cf Bonhote 1996) which has a different density than water and forms a bi-phasic system at room temperature but is miscible at higher temperatures.

It will be appreciated that the invention provides a method and apparatus that are simple and involve low risk of cross-contamination. They involve only low volumes, with simple, rapid and self-contained lysis.

The use of a chelating agent with a PNA probe is surprisingly advantageous. Many techniques won't work satisfactorily with a Chelex extraction, for example Restriction fragment length polymorphism. Chelex extraction is known to work in PCR because this can use single stranded and somewhat sheared DNA as a template. The small amount added (1:20) doesn't affect the PCR chemistry most of the time.

The simplicity of our embodiments, with minimal steps and a single tube extraction preventing loss of targets, rapidity, and the use of a chelating agent on a denser material such as a resin which means the nuclease co-factors and chelating agent are retained in the vessel are all clear advantages. The low ionic solution and high pH helps prevent NA binding to NA, including hairpins and loops, and ensures that any target NA is available to a probe. The low-ionic solution and high pH is traditionally considered a disadvantage to Chelex™ extractions and has limited its popularity in the field. However, in our invention this environment ensures that only the PNA probe, with its neutral backbone and resistance to high pH, can bind to the target. A standard DNA, RNA (or RNA derivative) probe will not bind to a target in these conditions, i.e. our assay is highly specific. Selective transport and storage of target NA by the paramagnetic beads would not be possible without the very unusual use of PNA probes with Chelex™, exploiting a feature which is ordinarily considered a distinct disadvantage of Chelex™.

A preferred embodiment of the invention involves the introduction of PNA probes prior to the introduction of the streptavidin-coated beads. This PNA is free to circulate in the lysate and bind to any target NA. This improves kinetics and speed of the procedure. This apparatus allows for maintenance of separation of the beads from the lysate and the biotinylated target until the appropriate time has elapsed. This is then accomplished by removal of a magnetic field, releasing the beads into the lysate. This allows control of the kinetics of the procedure without opening the tube.

The invention is not limited to the embodiments described. For example, the mechanism of using a chelating agent with PNA probes may be used in a more manual method without particular apparatus such as the apparatus 1. Also, it is not essential that the beads be embedded in wax. They could alternatively be provided lyophilised or in a gel plug. Also, it is not essential that the beads are removed from the vessel for analysis. In this case the analysis takes place in situ. The analysis means may for example be within the cap. In this case the magnetic mechanism may be arranged to convey the beads to an upper chamber for analysis, possibly through an annular passage in the support. These embodiments have the benefit of keeping everything within the same closed environment throughout.

Also, the apparatus of any embodiment may be used with samples having analytes other than NA, such as proteins, bacteria, or other microbiological entities.

The invention claimed is:

1. A method of preparing a nucleic acid sample for analysis with target enrichment, the method comprising the steps of:
   in a reaction vessel, lysing cells of the nucleic acid sample by heating said sample with a chelating agent to provide a crude lysate with a single-stranded target nucleic acid available for binding,
   providing a PNA probe in said crude lysate at a concentration sufficient for binding and capture of discernible levels of said target nucleic acid,
   providing magnetic or paramagnetic beads to which said PNA probe attach, said beads being in a solid plug of oil or wax,
   said heating heats said wax or oil in the reaction vessel due to applied heat for lysing so that the wax or oil becomes molten and the beads are free to mix in the sample while the molten wax or oil remains on the sample surface due to floating, said mixing in the sample providing intact bead-PNA probe-target nucleic acid complexes drawing the complexes magnetically through a fluid-fluid interface of said molten wax or oil; and
   moving said complexes through said molten wax or oil and into an analytical vessel, or
   solidifying said wax or oil with the bound bead-PNA probes-target nucleic acid complexes separated from the lysate and sealed within the solidified wax or oil,
   wherein the sample is heated with the chelating agent to provide a low ionic/high pH solution.

2. The method as claimed in claim 1, wherein the beads are in the size range of 50 nm to 5 μm.

3. The method as claimed in claim 1, wherein the PNA probe is in solution within the reaction vessel.

4. The method as claimed in claim 1, wherein the PNA probe and the crude lysate are brought into contact after the crude lysate cools to below a lysate annealing temperature; and wherein the lysing step is performed so that the target nucleic acid is sheared into fragments.

5. The method as claimed in claim 1, wherein the chelating agent concentration is in the range of 1% w/v to 20% w/v with respect to the sample; and wherein the chelating agent is a styrene-divinylbenzene co-polymer containing iminodiacetic acid groups.

6. The method as claimed in claim 1, wherein the heating is at a temperature of 70° C. to 99.5° C., for at least 5 minutes to provide a sample pH in the range of 10 to 11.

7. The method as claimed in claim 1, wherein an anion or cation of an ionic liquid has a functional group which is the chelating agent, in which the functional group captures target cations from an aqueous solution when the ionic liquid is water miscible, and in which a change in physical parameters changes the miscibility of the ionic liquid, and in which the ionic liquid, functional group and any captured target analyte is shifted between phases, providing for removal;
   wherein the anion or cation of the ionic liquid has a functional group which is the PNA probe, in which the functional group captures target nucleic acids from an aqueous solution when the ionic liquid is water miscible, and in which a change in physical parameters changes the miscibility of the ionic liquid, and in which the ionic liquid, functional group and any captured target analyte are shifted between phases in this manner, providing for extraction and purification of target analyte.

8. The method as claimed in claim 1, wherein the solid wax or oil is in a recess or a pocket at the lower end of an insert within the reaction vessel, said insert having an internal conduit within which a magnet is moved from a spaced-apart position to a position sufficiently close to the pocket so that it applies a magnetic field to move the beads.

9. The method as claimed in claim 1, wherein the molten wax or oil comprises a biphasic and thermomorphic body of molten wax or oil and water including an ionic liquid which varies in miscibility with water depending on a physical parameter.

10. The method as claimed in claim 9, wherein the physical parameter is a temperature or pH.

11. The method as claimed in claim 1, wherein the PNA probe is covalently bonded to the beads.

12. The method as claimed in claim 1, comprising the step of solidifying said wax or oil with the bound bead-PNA probes-target nucleic acid complexes separated from the lysate and sealed within the solidified wax or oil, and storing said solidified wax or oil for bio-banking.

13. A method of preparing a microbiological sample including a carrier liquid and a nucleic acid analyte, the method comprising the steps of:
   depositing the sample into a reaction vessel,
   holding at a surface of the sample a body of solid oil or wax with embedded paramagnetic or magnetic beads having a coating for attracting a PNA probe,
   heating the reaction vessel at a lower end of the reaction vessel to a level sufficient to lyse the sample,
   heating the wax or oil body so that the solid oil or wax becomes molten and the beads are free to mix in the sample, and
   applying a magnetic field to attract the beads to a support after incubation when the wax or oil body is molten.

14. The method as claimed in claim 13, comprising the step of removing the support from the reaction vessel to remove the beads as they are embedded in the wax or oil body after said body has re-solidified and/or because they are attracted to the support by a magnetic field; and wherein the heating to lyse the sample occurs at a position in the reaction vessel lower than the wax or oil plug, and said heating is sufficient to lyse the cells at a lower vessel level, and to melt the wax or oil at a higher vessel level; and comprising analysing the analyte without removing it from the reaction vessel of the support.

15. The method as claimed in claim 13, wherein the sample is heated with the chelating agent to provide a low ionic/high pH solution.

16. A microbiological sample preparation apparatus for preparing a nucleic acid sample for analysis with target enrichment, the apparatus comprising:
   a reaction vessel,
   a heater to heat the reaction vessel at a lower end of the reaction vessel to a level sufficient to lyse a sample with an analyte and a chelating agent in the reaction vessel, to provide a crude lysate available for binding,
   a PNA probe at a concentration sufficient for binding and capture of discernible levels of a target nucleic acid,
   a support holding a body of solid oil or wax with embedded paramagnetic or magnetic beads having a coating to which the PNA probe attach, said beads being in a solid plug of oil or wax, wherein the probe is immobilised on a surface of the support and/or the oil or wax body and/or the reaction vessel internal surface,
a magnetic device for applying a magnetic field to attract the beads to the support after incubation when the wax or oil body is molten, in which the magnetic device magnetically removes the beads with the attached PNA probe and bound target nucleic acid to draw them through a fluid-fluid interface of said molten wax or oil, and
the apparatus is configured
  so that said heating heats said wax or oil in the reaction vessel due to applied heat for lysing so that the wax or oil becomes molten and the beads are free to mix in the sample while the molten wax or oil remains on the sample surface due to floating, said mixing in the sample providing intact bead-PNA probe-target nucleic acid complexes drawing the complexes magnetically through said fluid-fluid interface of said molten wax or oil; and
  to move said complexes through said molten wax or oil and into an analytical vessel, or
  to solidify said wax or oil with the bound bead-PNA probes-target nucleic acid complexes separated from the lysate and sealed within the solidified wax or oil
wherein the sample is heated with the chelating agent to provide a low ionic/high pH solution.

17. The apparatus as claimed in claim 16, wherein the apparatus is configured for removing the support from the reaction vessel to remove the beads as they are embedded in the wax or oil body after said body has re-solidified and/or because they are attracted to the support by a magnetic field.

18. The apparatus as claimed in claim 16 wherein the magnetic device comprises a conduit within the support within which a magnet may be moved between a position proximate to the support lower end and a spaced-apart position.

19. The apparatus as claimed in claim 16, wherein the support has a pocket with a downwardly-facing open face within which the oil or wax body is engaged.

20. The apparatus as claimed in claim 16, wherein the apparatus comprises a device for analysing the analyte without removing the analyte; and wherein the support includes, at an upper end, said analysis device.

21. The apparatus as claimed in claim 16, wherein the apparatus comprises a device for analysing the analyte without removing the analyte; and wherein the support includes, at an upper end, said analysis device; wherein the analysis device includes a loop mediated amplification device and/or a capacitive sensor, and/or an optical sensor.

22. The apparatus as claimed in claims 16, wherein the support is a stem which is configured with a head for removing the sample from a material; wherein the stem comprises a tip with a recess, at least one receiver in a side wall of the recess, and a guide in the recess for pressing material radially into the receiver as the tip is pressed into the material; and wherein the guide is a distally-pointing spike and the receiver is an opening in the wall of the recess; and wherein the apparatus comprises an analysis vessel, the head is separable from the stem being joined by an interlock which requires a friction fit of interlocking solid parts with solid wax in-between, but melting of the wax causing separation so that the head drops to a bottom of the analysis vessel.

* * * * *